(12) United States Patent
Goss et al.

(10) Patent No.: US 12,315,610 B1
(45) Date of Patent: May 27, 2025

(54) HABIT-TRAINING DEVICE USING A FORCE-RESISTIVE SENSOR FOR SUBJECT DETECTION

(71) Applicants: Aaron Goss, Statesville, NC (US); William Black, Salisbury, NC (US)

(72) Inventors: Aaron Goss, Statesville, NC (US); William Black, Salisbury, NC (US)

( * ) Notice: Subject to any disclaimer, the term of this patent is extended or adjusted under 35 U.S.C. 154(b) by 0 days.

(21) Appl. No.: 18/627,698

(22) Filed: Apr. 5, 2024

(51) Int. Cl.
*G16H 40/67* (2018.01)
*G16H 20/00* (2018.01)

(52) U.S. Cl.
CPC ............. *G16H 20/00* (2018.01); *G16H 40/67* (2018.01)

(58) Field of Classification Search
CPC .. A61N 1/36564; A61N 1/375; A61N 1/3752; G16H 40/67; G16H 20/00
See application file for complete search history.

(56) References Cited

U.S. PATENT DOCUMENTS

2019/0117124 A1\* 4/2019 Hsu ...................... A61B 5/6892

\* cited by examiner

*Primary Examiner* — George Manuel
(74) *Attorney, Agent, or Firm* — The Rapacke Law Group, P.A.

(57) ABSTRACT

A habit-training device employing a force-resistive sensor for subject detection is disclosed, including a mat including one or more sensors to determine the presence of a child-weight individual in an environment. A speaker is provided in an environment to emit an audible cue to the child-weight individual, the audible cue to provide a reminder to perform a habit.

17 Claims, 4 Drawing Sheets

HABIT-TRAINING DEVICE USING A FORCE-RESISTIVE SENSOR FOR SUBJECT DETECTION

TECHNICAL FIELD

The embodiments disclosed herein generally relate to habit-training aids using a sensor to detect a subject and aid in the formation of a habit.

BACKGROUND

During adolescence, children receive various instructions from parents which aid in them in performing tasks and forming good habits. Parents often find it difficult to consistently provide timely reminders to their child. Few products exist which aid in developing positive habits through adolescence.

Force-resistive sensors include load cells to measure a force applied to the sensor. These sensors may be embedded in various devices to detect the presence of a force. In one use case, they may be utilized to detect the presence of an individual which is inferred upon by the detection of a force applied to the sensor.

SUMMARY OF THE INVENTION

This summary is provided to introduce a variety of concepts in a simplified form that is further disclosed in the detailed description of the embodiments. This summary is not intended for determining the scope of the claimed subject matter.

The embodiments provided herein relate to a habit-training device employing a force-resistive sensor for subject detection is disclosed, including a mat including one or more sensors to determine the presence of a child-weight individual in an environment. A speaker is provided in an environment to emit an audible cue to the child-weight individual, the audible cue to provide a reminder to perform a habit.

The habit-training system may involve delivering timely cues to remind a male child to lift and lower the toilet seat. To accomplish this, a mat is positioned on the floor near the toilet that is capable of detecting a child-weight individual standing at the toilet. Upon detecting such an individual, the device generates an audio and/or visual cue to remind the individual to lift the toilet seat prior to using the toilet. Further the device may generate a cue to flush and lower the toilet seat upon departure.

In another example, the habit-training system may involve delivering timely cues to remind a child to wash their hands. To accomplish this, the mat is positioned on the floor near the sink and detects the presence of the child near the sink. Upon detecting the child, the device generates an audible cue to remind the child to wash their hands.

Initially, the cues may help the child comply with parental toilet-use instruction by offering an in-the-moment reminder to comply. Over time, repetition helps the child develop a permanent habit. Similarly, the cues may help the child comply with parental hand-washing instruction by providing an in-the-moment audible reminder to comply.

In one aspect, the one or more sensors are each force-resistive sensors.

In one aspect, the one or more sensors include a voltage circuit divider in electrical communication with an amplifier and a NAND trigger.

In one aspect, the resistance is monitored using the voltage circuit divider, the amplifier and the NAND trigger to determine if an individual standing on the mat is a child-weight individual.

In one aspect, the speaker is in remote communication with the microcontroller to remotely receive an audio signal from the microcontroller.

In one aspect, the speaker is positioned in the environment remotely from the habit-training device.

In one aspect, the system includes an energy storage device to provide power to the habit-training device.

In one aspect, the one or more sensors are provided as a component of a piezoresistive film.

In one aspect, the piezoresistive film is positioned between a first conductive layer and a second conductive layer.

In one aspect, the first conductive layer and the second conductive layer are each flexible.

In one aspect, the microcontroller is in connection with an analog-digital converter to measure a force applied to the mat.

In one aspect, the system includes a computer system including an application program in communication with a user computing device. The application program is in communication, via a network, to the habit-training device to execute, via a process in communication with the application program, computer-readable instructions to establish operational protocols to aid in the formation of habits.

BRIEF DESCRIPTION OF THE DRAWINGS

A complete understanding of the present embodiments and the advantages and features thereof will be more readily understood by reference to the following detailed description when considered in conjunction with the accompanying drawings wherein.

DETAILED DESCRIPTION

Figure 1:
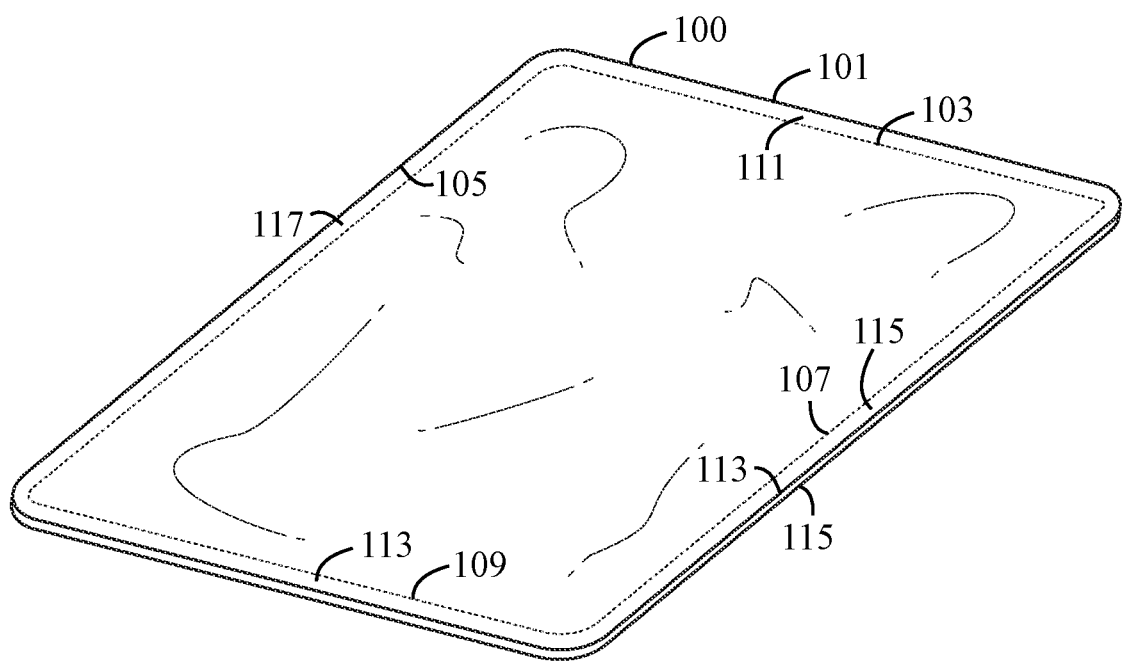
FIG. 1 illustrates a perspective view of the habit-forming device having at least one embedded force-resistive sensor, according to some embodiments.

The specific details of the single embodiment or variety of embodiments described herein are set forth in this application. Any specific details of the embodiments described herein are used for demonstration purposes only, and no unnecessary limitation(s) or inference(s) are to be understood or imputed therefrom.

Before describing in detail exemplary embodiments, it is noted that the embodiments reside primarily in combinations of components related to particular devices and systems. Accordingly, the device components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

In general, the embodiments provided herein relate to a device and method for helping children form healthy and/or useful habits. The device accomplishes this by detecting the presence of a child using one or more force-resistive sensors (or similar sensors) disposed within a mat or other surface whereon the child may stand. Once the child is detected, a visual and/or audio cue is emitted and/or displayed to help the child remember to perform location-specific actions. For example, the device may be positioned on the floor in a bathroom, such as near the toilet or near the sink. When a child-weight individual is detected standing on the device, a speaker plays an audio cue such as "Remember to lift the toilet seat." When the child-weight individual departs, the device can generate an additional cue such as "Remember to flush and lower the toilet seat."

Similarly, the device may be positioned to sense a child-weight individual near a sink. In this case, when the device senses the child-weight individual near the sink, an audio cue such as "Remember to wash your hands", or "remember to brush your teeth" may be played.

In another example, the habit-training device may be used during prayer to ensure the child engages in prayer activities. Force-resistive sensors may be disposed within the device to detect if the child is kneeling, rather than standing on the device, thus indicating the child is engaging in a prayer. In this example, once the child-weight individual is detected, the speaker may emit sounds which recite a prayer.

One skilled in the arts will readily understand that while various examples of a habit are described as use-case for the device, the device may be used for various use cases not mentioned herein. In such, the device can be programmed to play a customizable audio cue which can be changed depending on the habit being trained.

The device distinguishes between child-weight and adult-weight individuals by using a sensor array or a single sensor to detect whether an individual is present. The sensor(s) are programmed to reliably differentiate between a child standing on the device, and an adult standing on the device. Avoiding false triggers when adults are standing on the device is important to the success of the device because adults might remove the device or permanently deactivate it if they are subjected to audio cues when they use the bathroom.

The process helps the child to form habits by generating timely audio cues to perform actions when the child is in the location where the habit is to be performed.

FIG. 1 illustrates a perspective view of the habit-training device 100. In the illustrated example, the habit-training device 100 is configured as a mat 101 which may be stood upon by an individual. One or more sensors 103 are provided within the habit-training device 100 or on a surface 105 of the habit-training device 100 to detect the presence of a subject standing on the device and determine if the subject is a child-weight individual. The sensors 103 may be force-resistive sensors 107 or similar sensors which can detect the weight and presence of the subject.

In some embodiments, the habit-training device 100 includes an electrically conductive, piezoresistive film 109 layer to create a thin mat 101 with a large surface area that acts as a weight sensor to detect when the weight of a subject standing on the mat 101. Conductors 111,113,115,117 (or an array of conductors to improve precision) are attached to each side of the film to measure applied force via change in resistance to the film 109. Once weight is applied to the mat 101 the device 100 generates a cue or cues consisting of audio and/or visual elements (for example a recorded voice) to help in the subject forming a habit. In such, the user is cued to perform certain actions while in an environment.

In some embodiments, the habit-training device 100 may be configured as various types of mats including bathroom mats, shower mats, kitchen mats, yoga mats, prayer mats, and others which the user may stand on, such that the individual can be identified as a child-weight individual, and adult, or other non-child-weight subject. The habit-training device 100 may include various textures, coatings, textile coverings, etc. depending on a general use-case for the mat 101. For example, the habit-training device 100 may be covered with a towel-like textile to provide a pleasant and absorbent surface in the use-case wherein the habit-training device 100 is positioned in a bathroom environment. In another example, the habit-training device 100 may be able to be positioned within a cover, such that it may be moved into and out of various covers which may be advantageous for different use-cases (e.g., disposing the habit-training device 100 within a towel-like cover for use in the bathroom, and a yoga-mat-type cover for use within a yoga mat).

In some embodiments, the mat 101 includes piezoresistive film in connection with a circuit comprised of a voltage divider, operational amplifier, and Negative AND (NAND) trigger which greatly reduces power requirements from a milliwatt scale to a microwatts scale. The piezoresistive film allows the mat 101 to be flexible rather than rigid.

In some embodiments, the piezoresistive film 111 is provided between a first conductive layer 113 and a second conductive layer 115. Resistance between the conductive layers 113,115 is monitored by a voltage divider, operational amplifier and NAND trigger. When resistance drops below a threshold value, visual and/or audio cues are activated and/or a microcontroller may be activated to control cues to the user. Further, the microcontroller may be used in connection with an analog-digital converter to measure the amount of force applied to the mat 101.

The device also has industrial and commercial applications as a low-power, weight-triggered trip sensor. Using a voltage-divider circuit with an operational amplifier and NAND trigger, the mat can be monitored with power consumption of only a few microwatts.

The mat can be fully sealed in nonconductive rubber or plastic, rendering it safe and easy to clean in bathroom and industrial environments.

Although the mat will be flexible in its primary configuration, an alternate configuration includes a stiffening layer that would improve the device's precision when placed on non-supportive flooring such as carpet.

Figure 2:
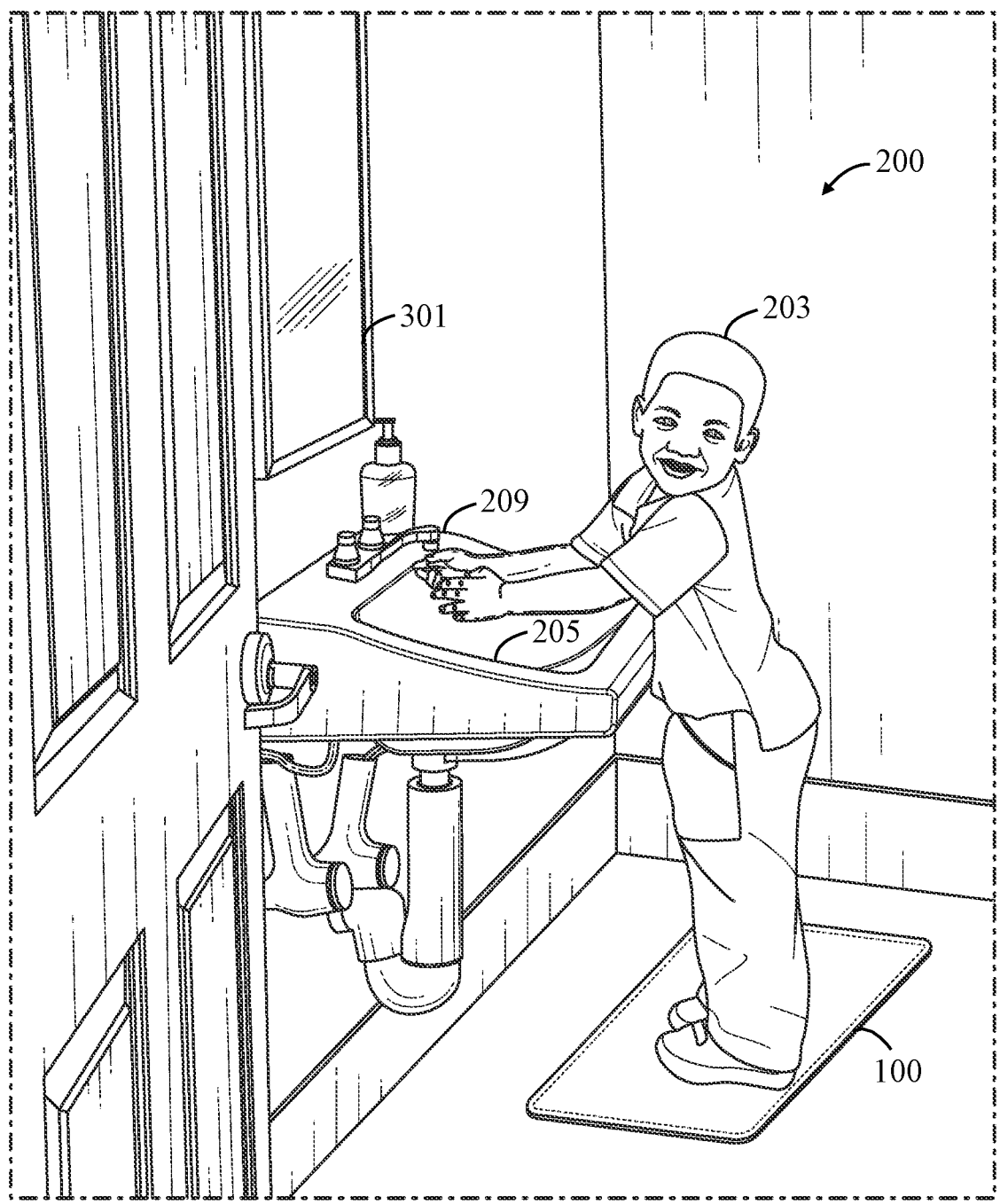
FIG. 2 illustrates a perspective view of the habit-training device positioned within an environment, wherein the habit-training device is positioned to sense the presence of a child, according to some embodiments.
Figure 3:
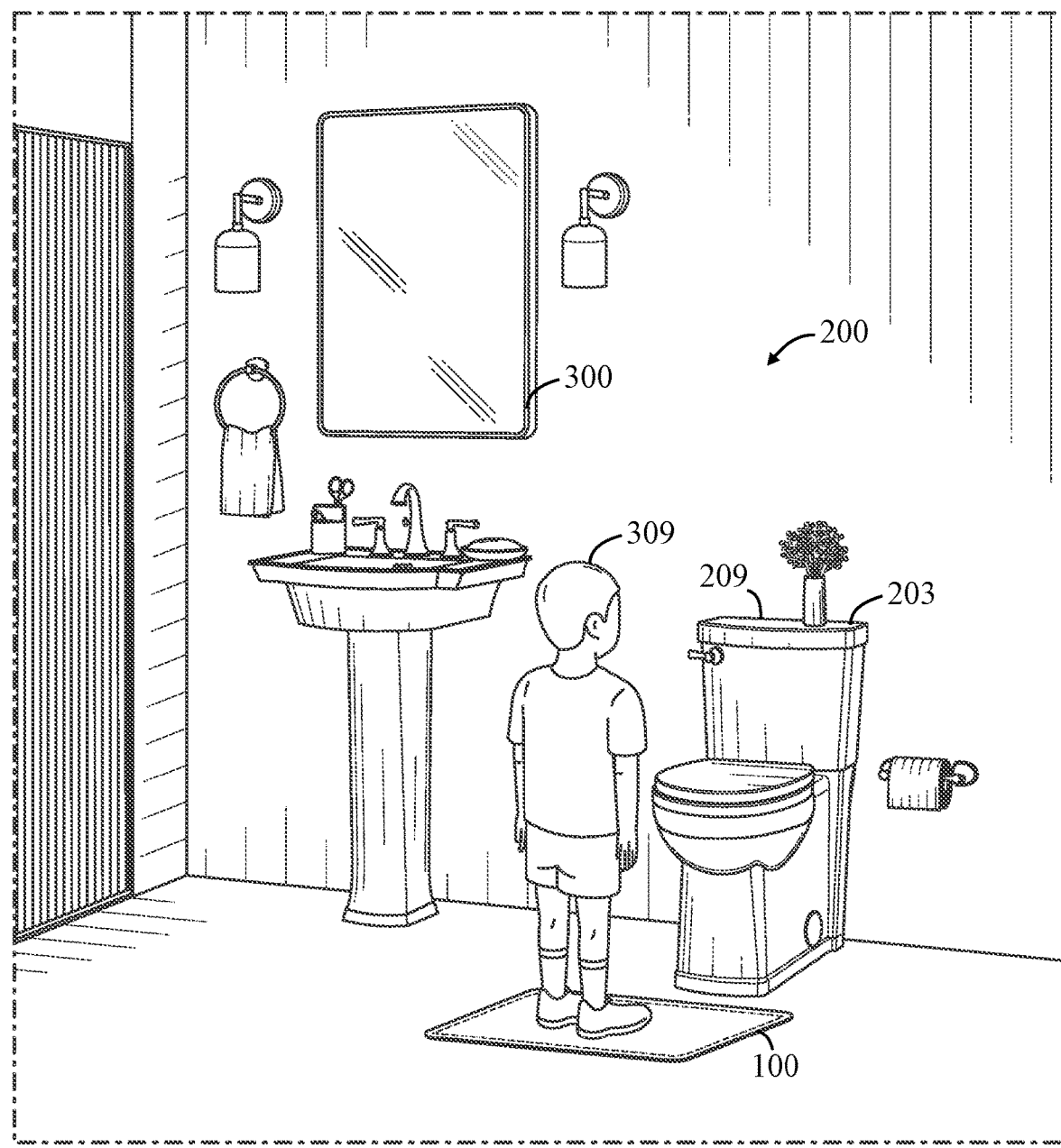
FIG. 3 illustrates a perspective view of the habit-training device positioned within an environment, wherein the habit-training device is positioned to sense the presence of a child, according to some embodiments.

FIG. 2 and FIG. 3 illustrate the habit-training device 100 being positioned in an environment 200 (such as a bathroom 301) to sense a child-weight individual 203 using a sink 205 (as shown in FIG. 2) or a toilet 309 (as shown in FIG. 3). The device 100 is shown positioned on the ground such that the force-resistive sensors are able to detect the presence of individuals in the environment 200 and differentiate between the weight of an adult and the weight of a child. The sensors are specifically configured to determine if the individual is a child-weight individual, thus indicating that a child is present and utilizing one or more fixtures 209 in the environment.

If the device 100 is positioned in an environment wherein the use fixtures and the habits associated with them is not appropriate, the force-resistive sensors can be used to detect the presence of the child in a particular area of the environment, the anatomical position of the child (i.e., is the child kneeling), etc.

The term "fixtures" is used herein to describe appliances, tools, utensils, or other items which the child-weight individual may interact with. In the illustrated examples, the fixtures include a sink and a toilet.

In some embodiments, the device 100 may include multiple speakers to emit a louder, or more room-filling audio cue.

In some embodiments, the device 100 may be hardwired to a power source. In such, the device 100 may not need to be charged.

Figure 4:
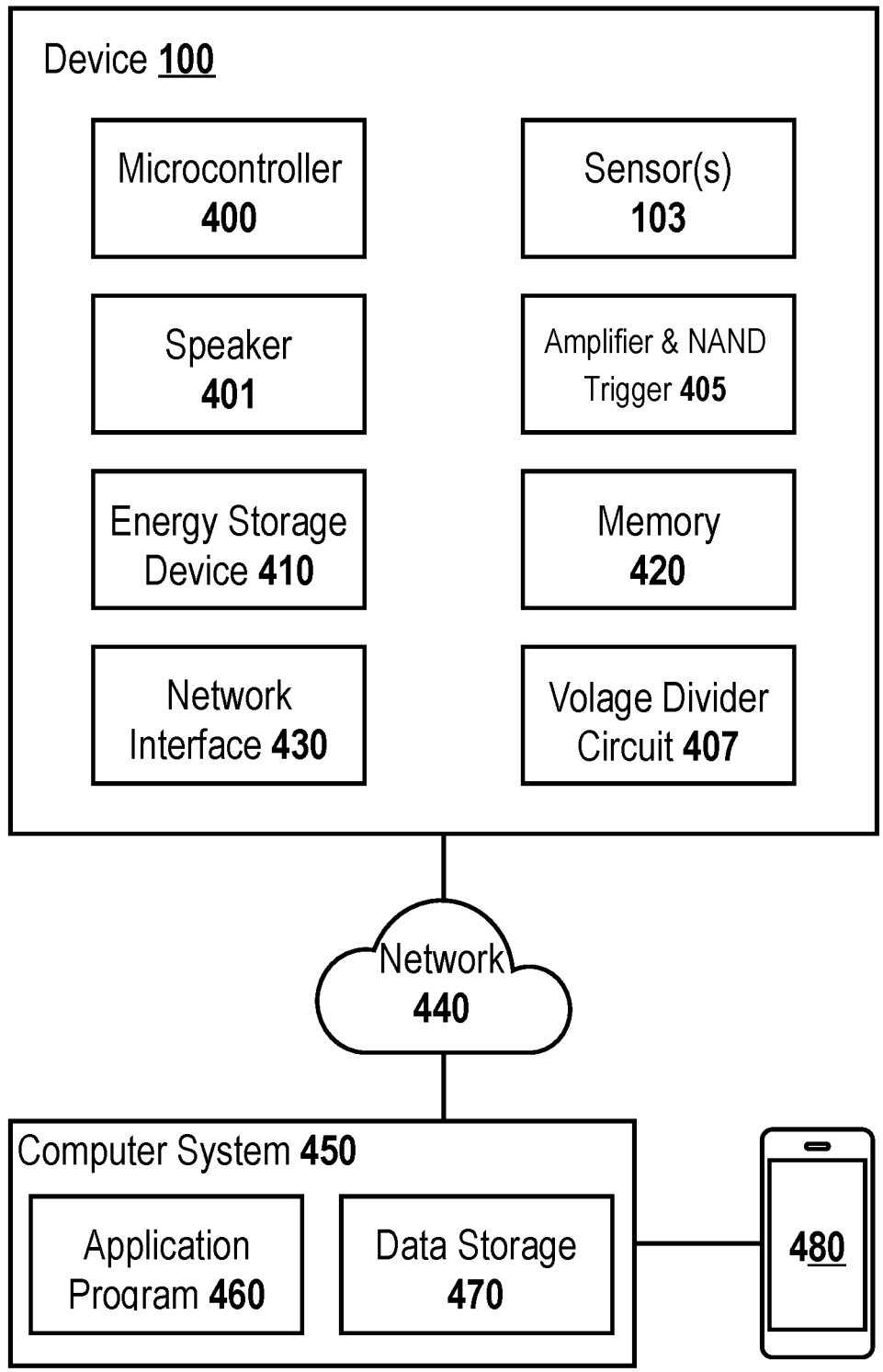
FIG. 4 illustrates a block diagram of the system infrastructure, according to some embodiments.

FIG. 4 illustrates a block diagram of the components of the device 100, and specifically shows the electrical components which provide functionality to the device 100. The device 100 is in electrical communication with a microcontroller 400, speaker 401, force-resistive sensor(s) 103, voltage divider circuit 407, energy storage device 410, amplifier and NAND trigger 405, network interface 430, and memory 420. The energy storage device 410 can be a rechargeable battery, or other energy storage device to supply power to the device 100. The microcontroller 400 communicates with the memory 420 which stores operational instructions for the device functions. The speaker 401 may be positioned on the device 100 or within the environment and communicate with the device 100 remote communication protocols such as Bluetooth or other NFC means of communicating. The speakers 401 may also be wired to the device 100.

Resistance between the conductive layers is monitored by a voltage divider circuit 407, operational amplifier and NAND trigger 405. When resistance drops below a threshold value, visual and/or audio cues are activated and/or the microcontroller 400 and may be activated to control cues to the user. Further, the microcontroller 400 may be used in connection with an analog-digital converter to measure the amount of force applied to the mat 101.

The device 100 is in communication with a computer system 450 via a network 440. In another embodiment, the device 100 communicates with the computer system 450 via a hardwired connection such as a USB cable or similar device. The computer system 450 is operable on a user computing device 480 capable of operating the application program 460 capable of executing instructions stored in the data storage 470.

In some embodiments, the application program 460 is capable of allowing the user to input various instructions via the user computing device 480 and control the functionality of the device remotely. For example, the user may utilize their smartphone to input a habit, select and/or record an audio message to be played on the speakers 401, adjust child weight settings, etc.

In some embodiments, the computer system 400 includes one or more processors coupled to a memory 420 through a system bus that couples various system components, such as a user interface, to the processors. The bus may be any of several types of bus structures including a memory bus or memory controller, a peripheral bus, and a local bus using any of a variety of bus architectures. For example, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

In some embodiments, the computer system 450 includes one or more input/output (I/O) devices, such as video device(s) (e.g., a camera), audio device(s), and display(s) are in operable communication with the computer system 450. In some embodiments, similar I/O devices may be separate from the computer system 450 and may interact with one or more nodes of the computer system 450 through a wired or wireless connection, such as over a network interface.

Processors suitable for the execution of computer readable program instructions include both general and special purpose microprocessors and any one or more processors of any digital computing device. For example, each processor may be a single processing unit or a number of processing units and may include single or multiple computing units or multiple processing cores. The processor(s) can be implemented as one or more microprocessors, microcomputers, microcontrollers, digital signal processors, central processing units, state machines, logic circuitries, and/or any devices that manipulate signals based on operational instructions. For example, the processor(s) may be one or more hardware processors and/or logic circuits of any suitable type specifically programmed or configured to execute the algorithms and processes described herein. The processor(s) can be configured to fetch and execute computer readable program instructions stored in the computer-readable media, which can program the processor(s) to perform the functions described herein.

In this disclosure, the term "processor" can refer to substantially any computing processing unit or device, including single-core processors, single-processors with software multithreading execution capability, multi-core processors, multi-core processors with software multi-threading execution capability, multi-core processors with hardware multithread technology, parallel platforms, and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures, such as molecular and quantum-dot based transistors, switches, and gates, to optimize space usage or enhance performance of user equipment. A processor can also be implemented as a combination of computing processing units.

In some embodiments, the memory 420 includes computer-readable application instructions provided by the application program 460, configured to implement certain embodiments described herein, and a data storage 470, comprising various data accessible by the application instructions. In some embodiments, the application instructions include software elements corresponding to one or more of the various embodiments described herein. For example, application instructions may be implemented in various embodiments using any desired programming language, scripting language, or combination of programming and/or scripting languages (e.g., Android, C, C++, C#, JAVA, JAVASCRIPT, PERL, etc.).

In this disclosure, terms "store," "storage," "data store," data storage," "database," and substantially any other information storage component relevant to operation and functionality of a component are utilized to refer to "memory components," which are entities embodied in a "memory," or components comprising a memory. Those skilled in the art would appreciate that the memory and/or memory components described herein can be volatile memory, nonvolatile memory, or both volatile and nonvolatile memory. Nonvolatile memory can include, for example, read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include, for example, RAM, which can act as external cache memory. The memory and/or memory components of the systems or computer-implemented methods can include the foregoing or other suitable types of memory.

Generally, a computing device will also include, or be operatively coupled to receive data from or transfer data to, or both, one or more mass data storage devices; however, a computing device need not have such devices. The computer readable storage medium (or media) can be a tangible device that can retain and store instructions for use by an instruction execution device. The computer readable storage medium can be, for example, an electronic storage device, a magnetic storage device, an optical storage device, an electromagnetic storage device, a semiconductor storage device, or any suitable combination of the foregoing. A non-exhaustive list of more specific examples of the computer readable storage medium can include: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. In this disclosure, a computer readable storage medium is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

In some embodiments, the steps and actions of the application instructions enabled by the application program 460 described herein are embodied directly in hardware, in a software module executed by a processor, or in a combination of the two. A software module may reside in RAM, flash memory, ROM memory, EPROM memory, EEPROM memory, registers, a hard disk, a removable disk, a CD-ROM, or any other form of storage medium known in the art. An exemplary storage medium may be coupled to the processor 110 such that the processor 110 can read information from, and write information to, the storage medium. In the alternative, the storage medium may be integrated into the processor 110. Further, in some embodiments, the processor 110 and the storage medium may reside in an Application Specific Integrated Circuit (ASIC). In the alternative, the processor and the storage medium may reside as discrete components in a computing device. Additionally, in some embodiments, the events or actions of a method or algorithm may reside as one or any combination or set of codes and instructions on a machine-readable medium or computer-readable medium, which may be incorporated into a computer program product.

In some embodiments, the application instructions for carrying out operations of the present disclosure can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The application instructions can execute entirely on the user's computer, partly on the user's computer, as a stand-alone software package, partly on the user's computer and partly on a remote computer, or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present disclosure.

In some embodiments, the application instructions can be downloaded to a computing/processing device from a computer readable storage medium, or to an external computer or external storage device via a network 440. A network adapter card or network interface in each computing/processing device receives computer readable program instructions from the network and forwards the computer readable application instructions for storage in a computer readable storage medium within the respective computing/processing device.

In some embodiments, the computer system 450 includes one or more network interfaces 430 that allow the computer system 450 to interact with other systems, devices, or computing environments. In some embodiments, the computer system 450 comprises a network interface 430 to communicate with a network 440. In some embodiments, the network interface 430 is configured to allow data to be exchanged between the computer system 100 and other devices attached to the network 440, such as other computer systems, or between nodes of the computer system 450. In various embodiments, the network interface 430 may support communication via wired or wireless general data networks, such as any suitable type of Ethernet network, for example, via telecommunications/telephony networks such as analog voice networks or digital fiber communications networks, via storage area networks such as Fiber Channel SANs, or via any other suitable type of network and/or protocol.

In some embodiments, the network 440 corresponds to a local area network (LAN), wide area network (WAN), the Internet, a direct peer-to-peer network (e.g., device to device Wi-Fi, Bluetooth, etc.), and/or an indirect peer-to-peer network (e.g., devices communicating through a server, router, or other network device). The network 440 can comprise copper transmission cables, optical transmission fibers, wireless transmission, routers, firewalls, switches, gateway computers and/or edge servers. The network 440 can represent a single network or multiple networks. In some embodiments, the network 440 used by the various devices of the computer system 100 is selected based on the proximity of the devices to one another or some other factor. For example, when a first user device and second user device are near each other (e.g., within a threshold distance, within direct communication range, etc.), the first user device may exchange data using a direct peer-to-peer network. But when the first user device and the second user device are not near each other, the first user device and the second user device may exchange data using a peer-to-peer network (e.g., the Internet). The Internet refers to the specific collection of networks and routers communicating using an Internet Protocol ("IP") including higher level protocols, such as Transmission Control Protocol/Internet Protocol ("TCP/IP") or the Uniform Datagram Packet/Internet Protocol ("UDP/IP").

In some embodiments, the system is world-wide-web (www) based, and the network server is a web server delivering HTML, XML, etc., web pages to the computing devices. In other embodiments, a client-server architecture may be implemented, in which a network server executes enterprise and custom software, exchanging data with custom client applications running on the computing device.

In some embodiments, the system can also be implemented in cloud computing environments. In this context, "cloud computing" refers to a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

In some embodiments, the device consists of two ultrasonic oscillator/receiver pairs, wired to a microcontroller along with a speaker, powered by a battery pack. These elements are installed in an aesthetic housing. The housing mounts to the wall via prismatic bracket, or similar mounting system.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety to the extent allowed by applicable law and regulations. The systems and methods described herein may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

Many different embodiments have been disclosed herein, in connection with the above description and the drawings. It will be understood that it would be unduly repetitious and obfuscating to literally describe and illustrate every combination and subcombination of these embodiments. Accordingly, all embodiments can be combined in any way and/or combination, and the present specification, including the drawings, shall be construed to constitute a complete written description of all combinations and subcombinations of the embodiments described herein, and of the manner and process of making and using them, and shall support claims to any such combination or subcombination.

The foregoing is provided for purposes of illustrating, explaining, and describing embodiments of this disclosure. Modifications and adaptations to these embodiments will be apparent to those skilled in the art and may be made without departing from the scope or spirit of this disclosure.

As used herein and in the appended claims, the singular forms "a", "an", and "the" include plural referents unless the context clearly dictates otherwise.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

In many instances entities are described herein as being coupled to other entities. It should be understood that the terms "coupled" and "connected" (or any of their forms) are used interchangeably herein and, in both cases, are generic to the direct coupling of two entities (without any non-negligible (e.g., parasitic intervening entities) and the indirect coupling of two entities (with one or more non-negligible intervening entities). Where entities are shown as being directly coupled together or described as coupled together without description of any intervening entity, it should be understood that those entities can be indirectly coupled together as well unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

An equivalent substitution of two or more elements can be made for any one of the elements in the claims below or that a single element can be substituted for two or more elements in a claim. Although elements can be described above as acting in certain combinations and even initially claimed as such, it is to be expressly understood that one or more elements from a claimed combination can in some cases be excised from the combination and that the claimed combination can be directed to a subcombination or variation of a subcombination.

It will be appreciated by persons skilled in the art that the present embodiment is not limited to what has been particularly shown and described herein. A variety of modifications and variations are possible in light of the above teachings without departing from the following claims.

What is claimed is:

1. A habit-training device employing a force-resistive sensor for subject detection, the device comprising:

a mat including one or more sensors to determine the presence of a child-weight individual in an environment; and a speaker to emit an audible cue to the child-weight individual, the audible cue to provide a reminder to perform a habit, wherein the one or more sensors are each force resistive sensors and wherein the one or more sensors include a voltage circuit divider in electrical communication with an amplifier and a NAND trigger.

2. The habit-training device of claim 1, wherein if the resistance is monitored using the voltage circuit divider, the amplifier and the NAND trigger to determine if an individual standing on the mat is a child-weight individual.

3. The habit-training device of claim 2, wherein the speaker is positioned in the environment remotely from the habit-training device.

4. The habit-training device of claim 1, wherein the speaker is in remote communication with a microcontroller to remotely receive an audio signal from the microcontroller.

5. The habit-training device of claim 1, further comprising an energy storage device to provide power to the habit-training device.

6. The habit-training device of claim 1, wherein the one or more sensors are provided as a component of a piezoresistive film.

7. The habit-training device of claim 6, wherein the piezoresistive film is positioned between a first conductive layer and a second conductive layer.

8. The habit-training device of claim 7, wherein the first conductive layer and the second conductive layer are each flexible.

9. The habit-training device of claim 8, further comprising a microcontroller in connection with an analog-digital converter to measure a force applied to the mat.

10. A system for facilitating the formation of positive habits via a habit-training device including a force-resistive sensor, the system comprising:
   a mat including one or more sensors to determine the presence of a child-weight individual in an environment, the one or more sensors each being force-resistive sensors provided on a piezoresistive film disposed between a first conductive layer and a second conductive layer;
   a voltage circuit divider, and an amplifier and a NAND trigger to monitor a resistance to determine if an individual standing on the mat is a child-weight individual by determining if the resistance drops below a threshold value;
   a speaker to emit an audible cue to the child-weight individual, the audible cue to provide a reminder to perform a habit, wherein the speaker is in remote communication with a microcontroller to remotely receive an audio signal from the microcontroller; and
   a computer system including an application program in communication with a user computing device, the application program in communication, via a network, to the habit training device to execute, via a process in communication with the application program, computer-readable instructions to establish operational protocols to aid in the formation of habits.

11. The system of claim 10, further comprising a memory to store the operational protocols.

12. The habit-training device of claim 10, wherein the speaker is positioned in the environment remotely from the habit-training device.

13. The habit-training device of claim 10, further comprising an energy storage device to provide power to the habit-training device.

14. The habit-training device of claim 10, wherein the first conductive layer and the second conductive layer are each flexible.

15. The habit-training device of claim 10, wherein the microcontroller is in connection with an analog-digital converter to measure a force applied to the mat.

16. The habit-training device of claim 10, wherein the application program permits a user to record the audible cue via a user computing device.

17. A system for facilitating the formation of positive habits via a habit-training device including a force-resistive sensor, the system comprising:
   a waterproof flexible mat including one or more sensors to determine the presence of a child-weight individual in an environment, the one or more sensors each being force-resistive sensors provided on a piezoresistive film disposed between a first conductive layer and a second conductive layer, the flexible mat provided with a textured or absorbent surface;
   a voltage circuit divider, and an amplifier and a NAND trigger to monitor a resistance to determine if an individual standing on the mat is a child-weight individual by determining if the resistance drops below a threshold value; a speaker to emit an audible cue to the child-weight individual, the audible cue to provide a reminder to perform a habit, the speaker positioned remotely from the waterproof flexible mat to emit the audible cue in the environment in which the child-weight individual is present; and a computer system including an application program in communication with a user computing device, the application program in communication, via a network, to the habit training device to execute, via a process in communication with the application program, computer-readable instructions to establish operational protocols to aid in the formation of habits, the application program to permit a user to record the audible cue.

* * * * *